United States Patent [19]
Borghi

[11] Patent Number: 6,033,434
[45] Date of Patent: Mar. 7, 2000

[54] BIFURCATED ENDOVASCULAR STENT AND METHODS FOR FORMING AND PLACING

[75] Inventor: Enzo Borghi, Budrio, Italy

[73] Assignee: Ave Galway Limited, Galway, Ireland

[21] Appl. No.: 08/945,464

[22] PCT Filed: Jun. 7, 1996

[86] PCT No.: PCT/IB96/00569

§ 371 Date: Nov. 20, 1997

§ 102(e) Date: Nov. 20, 1997

[87] PCT Pub. No.: WO96/41592

PCT Pub. Date: Dec. 27, 1996

[30] Foreign Application Priority Data

| Jun. 8, 1995 | [IT] | Italy | B095A0292 |
| Apr. 15, 1996 | [IT] | Italy | B096A0201 |
| Apr. 15, 1996 | [IT] | Italy | B096A0202 |

[51] Int. Cl.[7] ........................................ A61F 2/06
[52] U.S. Cl. ................................. 623/1; 623/12
[58] Field of Search .................. 623/1, 12, 901

[56] References Cited

U.S. PATENT DOCUMENTS

| 4,896,670 | 1/1990 | Crittenden . |
| 4,994,071 | 2/1991 | MacGregor . |
| 5,669,924 | 9/1997 | Shaknovich ............................ 623/1 X |
| 5,679,659 | 10/1997 | Verhoeven et al. ..................... 623/1 X |
| 5,725,572 | 3/1998 | Lam et al. ................................. 623/1 |
| 5,755,771 | 5/1998 | Penn et al. ................................. 623/1 |
| 5,766,238 | 6/1998 | Lau et al. .................................. 623/1 |
| 5,782,906 | 7/1998 | Marshall et al. .......................... 623/1 |
| 5,824,042 | 10/1998 | Lombardi et al. ........................ 623/1 |
| 5,824,043 | 10/1998 | Cottone, Jr. ............................... 623/1 |
| 5,824,056 | 10/1998 | Rosenberg ................................ 623/1 |
| 5,855,598 | 1/1999 | Pinchuk .................................... 623/1 |

FOREIGN PATENT DOCUMENTS

| 0421729 | 4/1991 | European Pat. Off. . |
| 0669114 | 8/1995 | European Pat. Off. . |
| WO9521592 | 8/1995 | WIPO . |

*Primary Examiner*—Jeffrey A. Smith
*Attorney, Agent, or Firm*—Sterne, Kessler, Goldstein & Fox P.L.L.C.

[57] ABSTRACT

A bifurcated endovascular stent is formed by a pair of tube-defining members, one of which is open at its ends and has a lateral opening between its ends. The other tubular structure is adapted to be advanced into one end of the first tube and exit through the lateral opening. The tube-defining members are formed in modular construction, each including an elongate spine and a plurality of generally tube defining modules attached to the spine in a longitudinally sequenced array. The modular construction enables a wide range of variations in the characteristics of the stent, including longitudinal flexibility, radial expansion among others.

39 Claims, 4 Drawing Sheets

BIFURCATED ENDOVASCULAR STENT AND METHODS FOR FORMING AND PLACING

BACKGROUND OF THE INVENTION

A number of medical procedures involve or can be supplemented with the placement of an endoluminal prostheses, commonly referred to as a stent, that can be implanted in a lumen, such as a blood vessel or other natural pathway of a patient's body. Such stents typically define a generally tubular configuration, and are expandable from a relatively small diameter (low profile) to an enlarged diameter. While in its low profile configuration, the stent is advanced endoluminally, by a delivery device, through the body lumen to the site where the stent is to be placed. The stent then can be expanded to a larger diameter in which it can firmly engage the inner wall of the body lumen. The delivery device then is removed, leaving the implanted stent in place. In that manner, the stent may serve to maintain open a blood vessel or other natural duct, the functioning of which had become impaired as a result of a pathological or traumatic occurrence.

Among the medical procedures in which stents have had increasing use is in connection with percutaneous transluminal angioplasty (PTA), and particularly percutaneous transluminal coronary angioplasty (PTCA). PTA and PTCA involve the insertion and manipulation of a dilating catheter through the patient's arteries to place the dilatation balloon of the catheter within an obstructed portion (stenosis) of a blood vessel. The balloon then is expanded forcibly within the obstruction to dilate that portion of the blood vessel thereby to restore blood flow through the blood vessel. Among the more significant complications that may result from such angioplasty is that in a significant number of cases, the dilated site again becomes obstructed. By placing a stent within the blood vessel at the treated site, the tendency for such restenosis may be reduced.

Stenoses often may develop in the branching region of a patient's blood vessel. Treatment of a stenosis in the branched region may present numerous additional difficulties in the design of devices to dilate stenoses at the branched region. Techniques and devices have been developed to effect a dilatation at a branched region such as the "kissing balloon" technique described in U.S. Pat. No. 4,896,670. The need for an effective stent that can be placed at a bifurcated region has been recognized; although it is believed that no such effective device has previously been developed.

A number of stents have been proposed and developed in the art, including single stents that define a single luminal pathway as well as bifurcated stents that define a branched pathway and are intended to be placed in a branching region of a blood vessel. The development of bifurcated stents, as compared to single stents presents numerous difficulties because of the branched arrangement and the difficulty in delivering and placing a bifurcated stent at the branched region of a blood vessel.

U.S. Pat. No. 4,994,071 (MacGregor) discloses a design for a bifurcating stent intended to be inserted into a bifurcated blood vessel. The stent is constructed from two lengths of continuous wire, one of which is formed in a series of interconnected loops to define a common tubular branch and one of the bifurcated branches. The other length of wire also is formed in a series of similarly interconnected loops to define the other branch of the bifurcation. The two assemblies of interconnected loops are connected together to define a Y-shaped structure. The interconnection between the structure defining the bifurcated branches is said to enable them to be bent to conform to the shape of the vessels into which the device is intended to be inserted. The loops are formed so that they can be expanded from an initial diameter to facilitate insertion into the blood vessel to an expanded, deployed diameter.

The MacGregor device presents a number of difficulties. Its continuous wire construction does not readily lend itself to precise matching to the vascular anatomy of pathological situation of the specific patient in whom the stent is to be placed. The construction is adapted, as a practical matter, only to be manufactured in standard configurations and lengths. When a standard length of stent does not ideally match the patient's anatomy, the physician would be forced to choose among the available standard lengths and configurations in an effort to make a selection that, at best, could be considered to be a compromise. A further difficulty with the device described in the MacGregor patent is that it is intended to be placed in the patient while it is maintained in its preformed Y-shaped configuration. Although the device is intended to be advanced and placed at the target site with its circumferential loops in a radially contracted configuration (low profile), advancement and insertion in that configuration could be expected to significantly complicate the delivery and placement procedure. The device is described as being placed by advancing it through a guide catheter so that the loops of the bifurcating stent do not engage the inner walls of the blood vessel. Consequently, it may not be possible to place the device in a narrow blood vessel, such as a coronary artery, that is too small to accommodate a guide catheter in addition to the other components of the device. Still another difficulty presented by the device is that it cannot be expected to present a readily visualized image under fluoroscopy or X-ray during implementation as well as at a later time. The MacGregor stent being formed from a pair of single slender wires may be difficult, if not impossible, to visualize under fluoroscopy or X-ray.

It is among the general objects of the invention to provide an improved bifurcated endovascular stent that overcomes the above-disadvantages.

SUMMARY OF THE INVENTION

In accordance with the invention, a bifurcated stent is constructed in a modular fashion to include at least two elongate spines and a plurality of generally tube-defining modules connected to at least one of the spines in a longitudinally sequenced array. Each module defines, in cooperation with its associated spine, a closed, ring-like structure, with the modules being aligned in an array to define a cage-like, generally tubular structure. Each of the modules may be formed from wire and is radially expandable from a reduced diameter, low profile configuration to an expanded diameter engageable with the inner luminal surface of the blood vessel or other body lumen. Each spine includes a longitudinal support wire to which the modules may be individually mounted in succession.

In one embodiment of the invention, the bifurcated stent is formed from two, initially independent single stents, each defining a single tubular configuration having its own array of modules connected to and extending along a spine. The modules on the two stents are constructed to enable the two stents to be combined, in situ, to form the bifurcate configuration. Each single stent may be considered to have a proximal group of modules and a distal group of modules. The modules in the proximal group of one single stent are spaced to enable them to be interfitted between similarly spaced modules on the proximal end of the other single stent. The device is placed at the bifurcation by first inserting one of the single stents to place its proximal group of modules in the common blood vessel and its distal group of modules in one of the branches of the blood vessel. The first placed stent is provided with a lateral opening between its ends. The first single stent is placed so that the lateral opening is positioned at the region of branching of the blood vessels to provide access to the branch vessel. The modules in the first place stent then are expanded to secure the first stent in place. The second single stent then can be advanced into the first stent and transversely through the lateral opening of the first stent to project the distal group of modules on the second stent to be advanced into the second branch of the blood vessel. With the second stent so placed, and with its proximal modules aligned with the spaces between modules of the proximal group on the first stent, the second stent can be expanded in place.

In another embodiment of the invention, a main longitudinal support wire of a single modular stent is connected at a junction, between its ends, to a branch longitudinal support wire. Radially expandable modules are connected to the main support wire both proximally and distally of the junction and to the branch support wire. The modules distally of the juncture of the support wires are spaced to be alternated so that the bifurcated segments of the stent can be brought together along a common axis with each other and with the axis of the modules proximally of the juncture. The bifurcated device thus may be compacted to a single tubular configuration with the bifurcated modules fitting in between each other in alternating fashion. In that configuration, the device can be delivered with a delivery catheter having a tubular sheath at its distal end to contain the compacted device. When the catheter is advanced to the deployment site, the sheath can be withdrawn to leave the device in place where it then can be expanded to stabilize its position in the blood vessel.

Among the objects of the invention is to provide an easily placeable bifurcated endovascular stent.

Another object of the invention is to provide a bifurcated stent that can be placed in the coronary arteries as well as other branched vessels.

Another object of the invention is to provide a bifurcated stent formed from single stents but that can be constructed in situ in the branched region of a patient's vasculature.

Another object of the invention is to provide an endovascular stent that is formed from two generally tubular members, at least one of which has a lateral opening between its ends to enable part of another stent to be passed partly through the first stent and laterally out of the opening.

An additional object of the invention is to provide a bifurcated stent in which the bifurcated portions of the stent can be brought together to lie along a common axis to facilitate insertion of the bifurcated stent into vascular anatomy.

Another object of the invention is to provide a bifurcated stent that can be custom tailored to the vascular anatomy of the patient in whom the device is to be implanted.

A further object of the invention is to provide a bifurcated vascular stent having good radiographic characteristics to facilitate its placement and subsequent visualization of the stent.

Another object of the invention is to provide a bifurcated stent construction that is modular.

DESCRIPTION OF THE DRAWINGS

The foregoing and other objects and advantages of the invention will be appreciated more fully from the following description thereof, with reference to the accompanying drawings wherein.

DESCRIPTION OF THE ILLUSTRATIVE EMBODIMENTS

Figure 1:
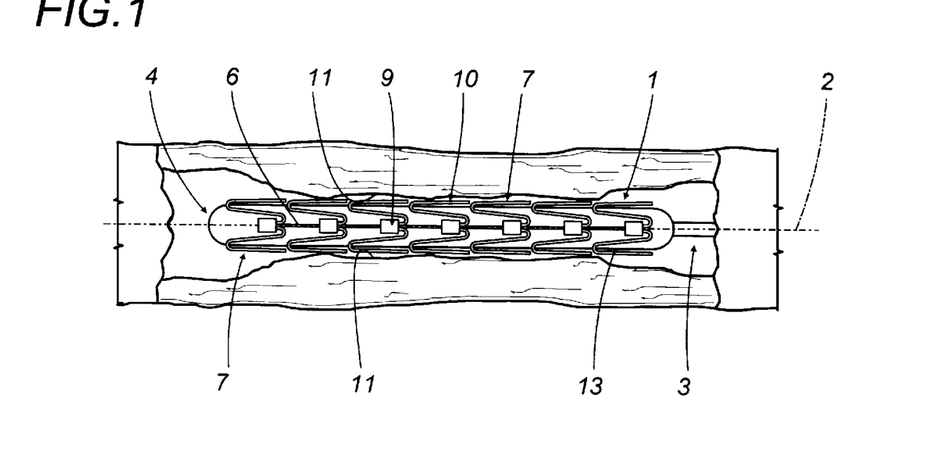
FIG. 1 is an illustration of a type of single modular tubular stent that may be used in the invention, disposed within a portion of a blood vessel with the stent in its low profile, unexpanded configuration.
Figure 2:
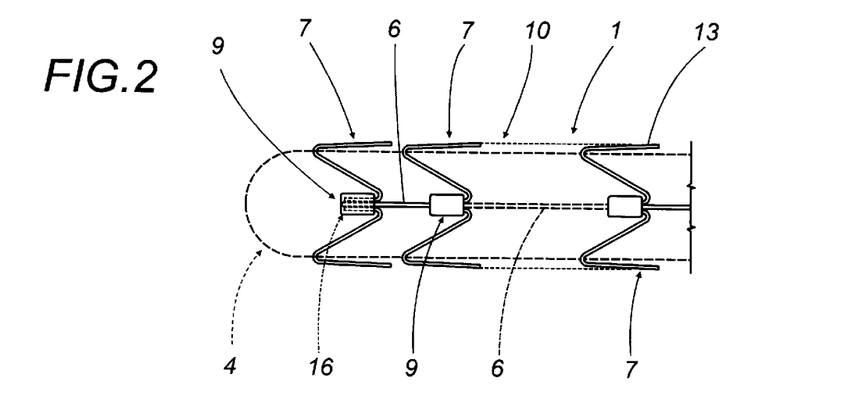
FIG. 2 is a somewhat diagrammatic illustration of the stent disposed on a balloon that has been inflated to expand the stent to a larger diameter.

FIG. 1 illustrates the type of modular endoprosthesis 1 (stent) that may be used in practicing the invention. The endoprosthesis may be considered to define a cage-like tubular arrangement formed from wire-like components and having a central longitudinal axis 2. The stent 1 is constructed from a plurality of individual modules 7 connected to each other along a spine that may be considered to include a longitudinal support wire 6 and connectors 9. The modules 7 are expandable from a contracted, low profile configuration, to facilitate placement of the stent in the body lumen, to an enlarged diameter, as suggested in FIG. 2, in which the modules can be brought into firm engagement with the inner surface of walls 11 of the body lumen 3 to maintain the body lumen open to facilitate blood flow. In the preferred embodiment, the modules are expandable inelastically. The radially expandable generally tubular modules 7 are mounted and aligned in longitudinally sequenced array on the support wire 6 by a connector 9 associated with each of the modules 7. The modules, when mounted on the support wire 6, may be considered to define a virtual peripheral surface 12 that, in transverse cross-section, is in the form of a virtual closed curve or loop 8 about the longitudinal axis 2.

Each module 7 is formed from a wire 13 shaped and configured to enable radial expansion of the cylindrical peripheral surface 12. The module may be formed by first forming the wire 13 into a flat serpentine configuration and then wrapping the serpentine wire into its looped configuration. The terminal ends 16 of the serpentine wire are free. The free ends 16 of the wire 13 may be attached to each other and to the support wire 6 by the connector 9. The serpentine arrangement of each of the modules may be considered to include a series of elongate segments alternated with and connected by bends that may be curved (e.g., circular) or may comprise shorter connective segments 15 connected to the elongate segments 14 at cusps 17. The connective bends between the longitudinal segments 14 may lie along and define a locus of the closed loop 8. Preferably, the wire 13 is formed so that the arrangement of bends will be uniformly circumferentially spaced about the virtual closed loop 8 to provide the modules 7 with uniform strength in directions transverse to the support wire 6.

Figure 3:
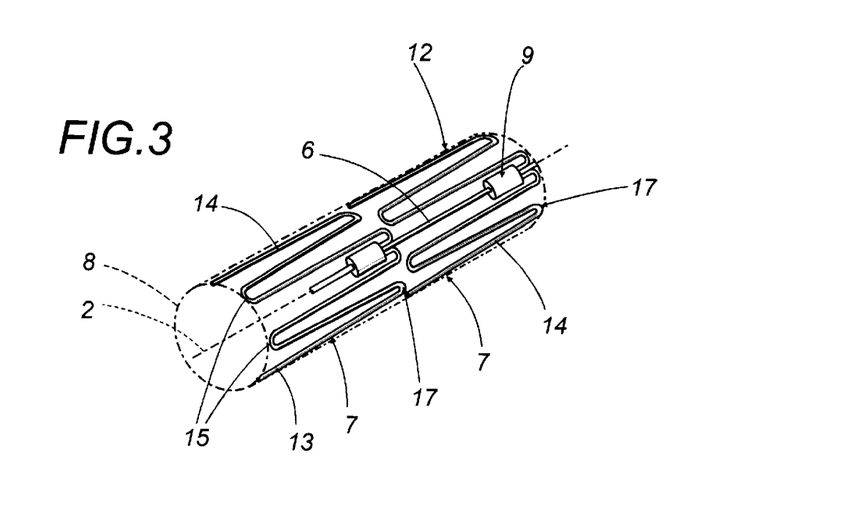
FIG. 3 is a somewhat diagrammatic illustration of a pair of adjacent modules of the stent illustrating their connection to the support wire.

As illustrated in FIG. 3 when the modules are in their low profile, unexpanded configuration, the bends 15, 17 that define the connection between adjacent longitudinal segments are such that the elongate segments 14 will lie substantially parallel to each other, defining an angle close to zero degrees. The angle will increase when the module is expanded. The configuration of the connective bends, including the cusps 17 may be varied to vary the angle or to vary their number circumferentially about the closed loop 8 to vary the characteristics of the modules 7, including varying its resistance to compressive radial loads such that the endoprosthesis can further be tailored and made to conform ideally to the specific body lumen 3 in which it is to be implanted.

By way of illustrative example only, a stent may be provided to include modules 7 formed from wire having a diameter of about 0.15 millimeter with elongate segments 14 (not including the connective bends between adjacent segments 14) of a length of about 1.8 millimeters. When the connective bends between adjacent elongate segments 14 are smoothly curved, they may have a radius of about 0.15 millimeter before expansion. A stent having the foregoing dimensions can be expected to be expandable to diameters between about 2.5 to about 4.0 millimeters without excessive expansion, and that such stent exhibits substantial resistance to radial collapse that is well above the maximum radial compressive loads and can be expected to be imposed on the stent by contraction of an artery having a luminal diameter of about 2.5 to about 4.0 millimeters.

In the preferred embodiment the connectors 9 may be constructed to be mounted on the longitudinal support wire 6 as by threading them on the wire 6. The connector 9 preferably may comprise a ring that defines sufficient internal space to receive and circumscribe the free ends 16 of the wire 13 while also permitting firm connection of the ring to the longitudinal support wire 6. The ring connector 9, free ends 16 of the wire and support wire 6 may be firmly connected by means of a permanent deformation, for example, by crimping, or may be attached to each other by spot welding. When assembled using laser spot welding, it is preferred that the terminal portions 16 of the module 7 are first welded to the ring 9 and the ring 9 then is welded to the support wire 6. In some instances, it may be desirable to modify the stent so that one or more of the modules (but not the endmost modules) are not securely attached to the support wire but, instead, are permitted some freedom of sliding movement along the support wire. This may enable making of a final adjustment to the position of the module after the device has been placed in the patient's blood vessel, should that be desired.

The rings may 9 be in the form of a relatively short segment of a tube receptive to the support wire 6 and the free ends 16 of the module 7. The internal surface of the ring 9 may be contoured to closely match the contour defined by the support wire 6 and free ends 16 that pass through the connectors 9.

The foregoing construction enables a stent to be specially assembled to conform precisely to the specific anatomy of the patient in whom the stent is to be placed. The modules can be positioned as desired along the support wire 6 and can be secured in that configuration. The support wire 6 may be selected to provide the desired degree of longitudinal flexibility and may be made from wire that is extremely flexible to facilitate positioning of the device in relatively inaccessible body lumen. With the foregoing construction in which the stent has an independent support wire 6, the degree of stiffness or flexibility of the support wire can be selected independently of the wire from which the tubular modules 7 are formed. The support wire 6 may be highly flexible to enable the stent to be carried through narrow, tortuous vessels, such as coronary arteries.

It should be understood that although the presently preferred embodiment of the invention incorporates a metal support wire 6 (e.g., stainless steel), the modular construction of the invention enables a fabrication of a stent in which the support wire may be formed from non-metallic materials, such as polymeric materials, for example, nylon. Other mechanically and biologically suitable classes of materials may be selected, including materials from among those that are biologically absorbable into the tissue of the vessel wall over time. With a bioabsorbable support wire 6, it should be selected to maintain its desirable mechanical characteristics for a sufficient time to enable the modules 7 to become firmly embedded in the vessel wall. Thus, the modular construction of the invention provides a substantially increased range of materials and properties for the individual components, each being selected to provide optimum results.

The connecting rings 9, especially when assembled about the two end segments 16 of the modules 7 and the support wire 6, present a significantly greater mass than that of the wire 13 from which the modules are fashioned. Thus, the region of the spine that includes the connecting rings 9 will present substantially greater radiopacity than that presented by the wire 13 of the associated module. The substantially increased radiopacity of the connected region enhances substantially the radiographic control of the endoprosthesis 1 during implantation. It also enables the prosthesis to be observed radiographically at a later time without requiring use of ultrasound procedures. The configuration of the stent enables the tubular frame 10 to be constructed to have a high mechanical strength while enabling expansion of the device between its low profile and maximum expanded configuration yet in which the wire 13 of the modules 7 will be substantially transparent to X-rays at radiation levels that are typically used in such procedures.

Figure 4:
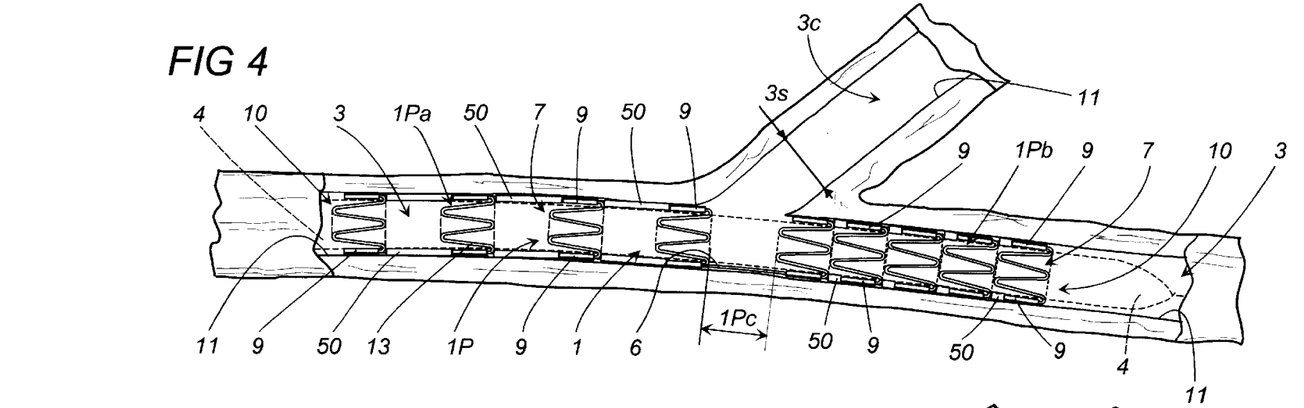
FIG. 4 is an illustration of a first single stent that forms a first component of one embodiment of a bifurcated stent and placed in a branched arterial region.
Figure 5:
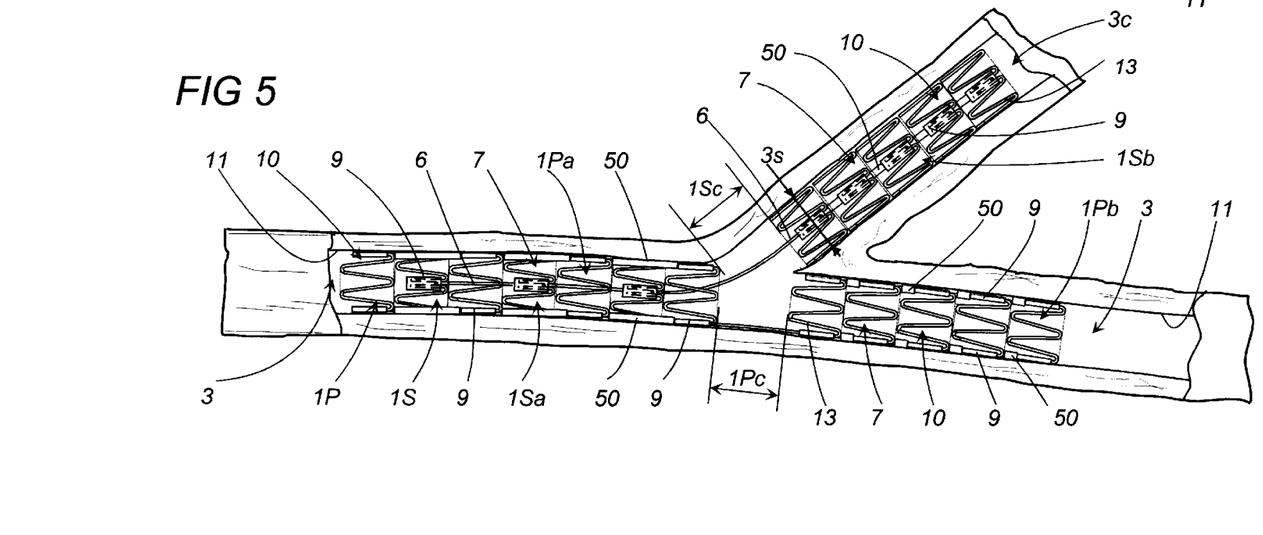
FIG. 5 is an illustration similar to FIG. 4 but with a second single stent having been placed in cooperative relation to the first single stent to form the bifurcated stent.

FIGS. 4 and 5 illustrate a further feature in which the invention can be provided with spacers 50 disposed between pairs of successive rings 9 before the rings are secured to the support wire 6. The spacers preferably are cylindrical in shape and have a central hole by which the spacers can be slid, in bead-like fashion, onto and along the longitudinal wire 6. When a series of connectors 9 and spacers 50 have been placed on the support wire 6, each successive pair of connectors 9 or spacers 50 may embrace one of the other. The length of the spacer(s) may be predetermined to enable precise control over the spacing between two successive modules as well as to reduce the risk of the support wire 6 being twisted or otherwise becoming damaged. An additional result that can be achieved by using the spacers 50 is that it enables a stent to be assembled with only the two endmost connectors 9 anchored securely to the support wire 6. In such an embodiment, the intermediate components (the connectors 9 and spacers 50) will be retained in position on the support wire and will not separate. Whether all or only the endmost connectors 9 are secured to the longitudinal support wire, the intermediate spacers need not be directly secured to the wire 6 but, instead, can be retained in place by and between their adjacent connectors 9. By way of dimensional example, the cylindrical spacers 50 that may be used with the device having the above-described dimensions may be about 1.10 millimeters in length, 0.30 millimeter in outer diameter and having a wall thickness of about 0.075 millimeter.

The spacers 50, being circular in cross-section may be arranged to lie substantially flush with the rounded outside face of the adjacent connecting elements.

A further advantage in the use of spacers 50 is that together with the rings and the portions of the wire that extend through the rings, the arrangement defines a spine that presents a substantially continuous elongate mass having a radiopacity considerably greater than that of the serpentine wires 13.

All components of the device should be formed from materials that are compatible with each other and will not form microcells that might give rise to electrochemical corrosion of any part of the device after it has been implanted into the blood vessel. The longitudinal support wire 6, wire 13 and connector 9 should have the same chemical composition. Exemplary materials that are preferable in making the endoprosthesis include those from the group of annealed stainless steels, titanium alloys, gold-nickel alloys, nickel-chromium alloys, and titanium-chromium alloys.

The support wire 6 and modules 7 may be treated and formed to vary the mechanical and functional characteristics independently of each other to obtain a desired configuration adapted to treat the anatomy of a specific patient. For example, the wire 13 from which the module is formed may be subjected to an annealing heat treatment to control the malleability of the wire.

Also among the characteristics of the invention is the manner in which the tubular modules 7 protect the balloon of a balloon catheter 4 (FIG. 1) used in the placement of the endoprosthesis 1. When the device is mounted on the folded balloon of the catheter and is in its low profile phase adapted for delivery, the elongate segments 14 will be disposed in close, substantially parallel proximity to each other circumferentially about the balloon. Additionally, to the extent that the individual tubular modules can be arranged in close longitudinal proximity to each other the balloon can be fully protected within the stent longitudinally as well as circumferentially. After the device and catheter 4 have been navigated to locate the deployment site, expansion of the device causes the elongate segments 14 to spread and expand circumferentially along the walls 11 to the body lumen 3 to wipe against the walls 11 and smooth surface roughness that may be present including, particularly, smoothing of sharp or hard regions that otherwise could damage the balloon and possibly result in balloon puncture. As the segments 14 of the module wipe against the walls 11 of the passage 3, they effect a significant shearing action.

FIGS. 4 and 5 illustrate the manner in which a bifurcated stent can be placed in branched blood vessels. In this embodiment, the bifurcated stent is formed from two single (i.e., non-bifurcated) stents 1P (FIGS. 4 and 5) and 1S (FIG. 5). The first single stent 1P may be constructed in the manner described above, to include an elongate spine to which a plurality of radially expandable modules 7 are attached. The modules 7 of the stent 1P may be considered to fall into groups, including a first group 1Pa that may be at the proximal end of the stent 1P and a second group 1Pb at the other end. The modules 7 in the first group 1Pa are spaced along the spine by a predetermined distance. As described in further detail below, the distance between the adjacent modules 7 in the first group 1Pa should be sufficient to enable the modules 7 of another stent to be fitted in between the modules 7 in the first group 1Pa. In the preferred embodiment, the predetermined distance is not less than the length of one module 7 measured along a direction parallel to the spine. The modules 7 in the second group 1Pb may be arranged in close longitudinal proximity to each other or other spacing should that may be appropriate for the particular branch of the vasculature into which it is to be placed. The first stent 1P also is constructed to define a space 1Pc between the first and second groups 1Pa, 1Pb of module 7 sufficient to enable a second single stent, in a low profile configuration, to be passed through the first stent (after expansion of the first stent) and protrude transversely out of the space 1Pc. By positioning the spaced region 1Pc at the juncture of the branched blood vessels, a second single stent can be advanced into the branched artery 3C. In a preferred embodiment, the length of the transverse opening 1Pc may be approximately that of the diameter of the cross-section 3S of the branch passage 3C.

The first stent 1P may be delivered to and placed in the artery by a delivery device having an expansion member that may include a balloon 4. The stent is mounted on the balloon 4 in a low profile.

The construction of the first stent 1P includes the arrangement of the spine that may be considered to be defined by the longitudinal support wire 6 and connectors 9. Spacers 50 also may be provided between adjacent pairs of connectors 9. The pattern of connectors 9 or connectors 9 and spacers 50, may be configured to permit distinct radiographic visualization of the space 1Pc at the intermediate portion of the stent to facilitate locating that portion at the desired place in the vascular branched region.

It may be noted that in the illustrative embodiment, the region of the transverse opening in the first stent 1P is radiographically distinguishable from the other portions of the stent. In the illustrative embodiment that is achieved by omitting spacers or other radiographically observable components along that portion of the spine that extends between the proximal and distal module groups 1Pa, 1Pb. Thus, the spine, in the region 1Pc, is defined only by the support wire 6 which has substantially less mass than the other portions of the spine so The second stent 1S may be of similar construction to the first stent 1P, including a first group 1Sa of module 7 spaced longitudinally to interfit with the spaces between the modules in the first group 1Pa of the first stent and a second stent 1Sb that may be arranged in close proximity to each other. The first and second groups 1Sa, 1Sb may be separated by a space 1Sc of a length approximating the diameter of the cross-section 3S of the branch passage 3C. The stent can be built in situ in the patient by first placing and expanding the first tubular member with the lateral opening in registry with one of the branches of the body lumen and then inserting the second tubular member through the first tubular member and laterally through the lateral opening and into the other branch lumen. The proximal ends of the tubular members are preferably configured to cooperate with each other to define a common single tube. The second stent is placed, as by a balloon delivery catheter, in the same manner as the first stent 1P, after at least the first group of modules 1Pa has been expanded into secure engagement with the inner surface of the blood vessel 3. The second stent is placed longitudinally within the vasculature so that the modules 7 of the proximal group 1Sa of the second stent is longitudinally aligned with the spaces between the modules 7 on the first group 1Pa of the first stent 1P. The relative positioning between the groups of modules may be facilitated by the radiopaque portions of the spine, particularly the region of the connectors 9 and, if employed, the spacers 50. With the modules of the first group 1Pa, 1Sa aligned, the modules 7 on the second group may be expanded. The resultant bifurcated stent structure may be configured to define a substantially continuous proximal stent portion within the blood vessel. Similarly, the second groups 1Pb, 1Sb of module 7 are expanded into firm engagement with the portions of the blood vessel branches in which they are placed.

It may be noted that the stents, either in the straight or bifurcated configuration, may be constructed with multiple spines. FIG. 4 illustrates an arrangement in which each of the segments 1Pa, 1Pb includes a second spine, circumferentially spaced about the virtual periphery 12 from the first spine. In this embodiment, each of the wires 13 of the modules 7 is formed to circumscribe about 180° of the loop defined by the module such that they can cooperate to define the generally cylindrical configuration. In the bifurcate embodiment as shown in FIGS. 4 and 5, it may be preferred to include the double spine configuration only along each of the groups 1Pa, 1Pb, omitting the wire 6 of the second spine at the intermediate region 1Pc where the second stent is intended to emerge transversely from the first stent. The inclusion of multiple spines may facilitate relative orientation of the first and second stents 1P, 1S when visualized radiographically.

Figure 6:
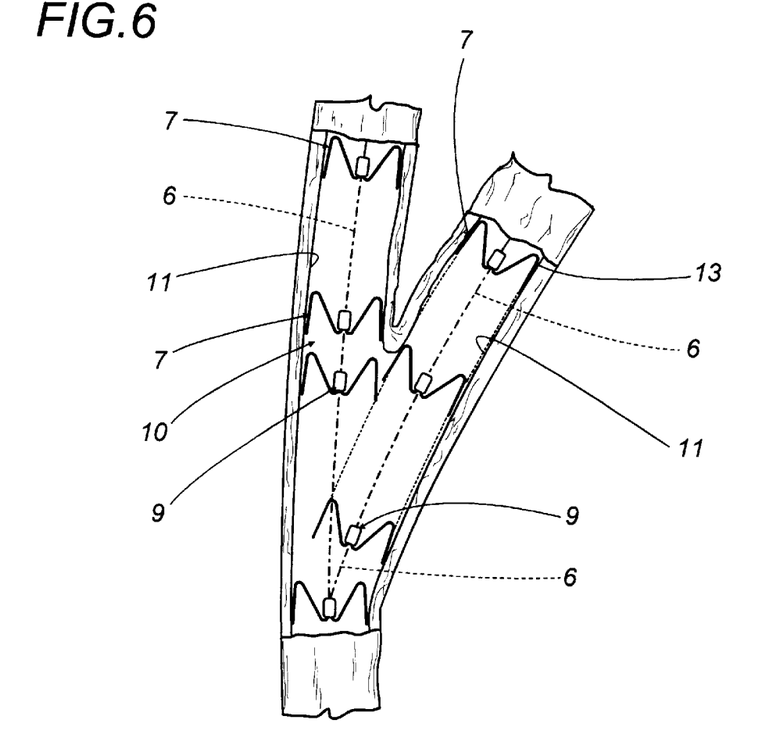
FIG. 6 is a somewhat diagrammatic illustration of another embodiment of a bifurcated stent in place within a bifurcated region of a blood vessel.

FIG. 6 shows another embodiment of a bifurcated stent that includes a tubular frame, indicated generally at 10 constructed with two longitudinal support wires 6, one of which is connected to an intermediate portion of the other by a connection such as the rings 9. The modules 7 are connected to their respective support wire 6 by connectors 9. The modules on the bifurcated portions of the stent are spaced along the support wire 6 so that they are disposed in alternating longitudinal positions to define sufficient space between a pair of adjacent modules on one branch to receive a module disposed on the other branch. By enabling the modules of the bifurcated branches to be interfitted in this manner, the two branches may be brought together along an axis generally in common with the axis of the unbranched portion thereby defining a single cylindrical structure that can be introduced into and advanced to the branched region of the patient's vasculature.

Figure 7:
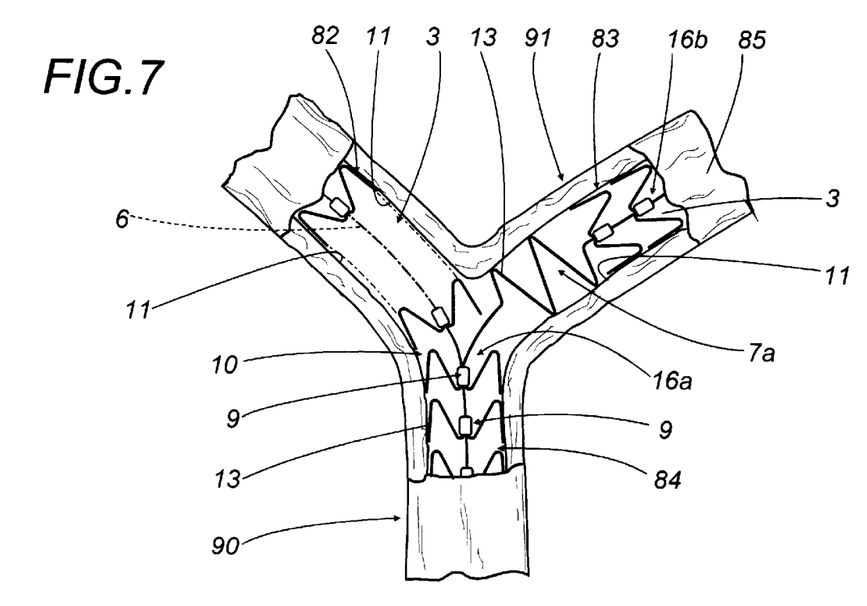
FIG. 7 is an illustration of a further modified embodiment of a bifurcated stent placed within a bifurcated vessel.

FIG. 7 illustrates still another embodiment of the invention in which a tubular frame 10 comprises a longitudinal support wire 6 to which a group 90 of modules 7 is connected. A second branching support wire 13 is connected to the support wire 6 at an end 16a by a connector 9. A second group 91 of modules is attached to the support wire 13. A portion of the support wire 13, indicated at 7a is constructed to enable the effective length of the wire 13 to be adjusted, toward or away from the juncture 16a. To that end, the portion 7a of the wire 13 may be formed in a helix or other longitudinally adjustable pattern. The modules 7 in the group 91 are attached to the support wire 13 distally of the region 7a. The arrangement of modules 7 carried by the support wire 6 includes the formation of sufficient gaps between selected modules into which the modules of the group 91 can be received. That enables the bifurcated device to be compacted into a single tubular structure having a single common axis that can be contained within a tubular sheath in order to deploy the device in the blood vessel.

Figure 8A:
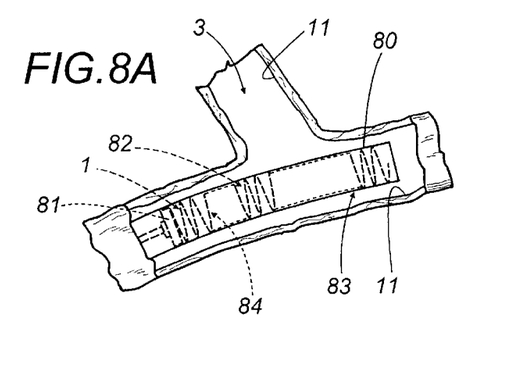
FIGS. 8(A)–8(E) illustrate, diagrammatically, the manner in which the bifurcated stent embodiments shown in FIGS. 6 and 7 may be deployed.
Figure 8B:
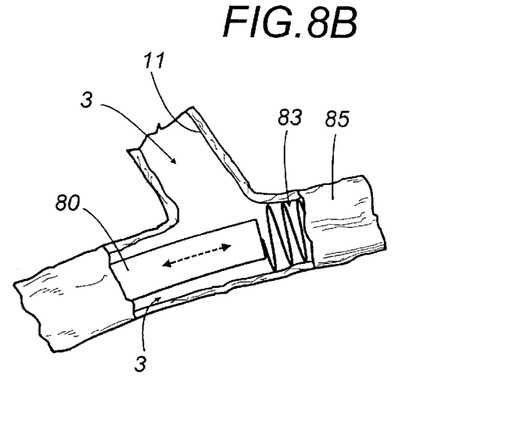
Figure 8C:
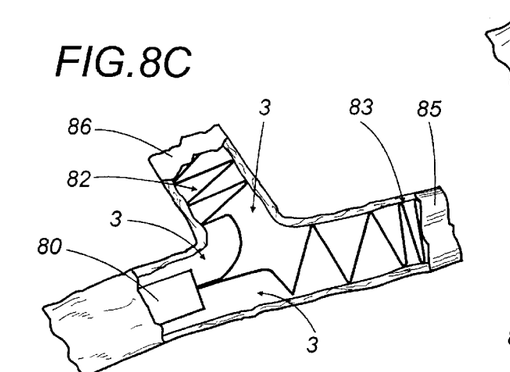
Figure 8D:
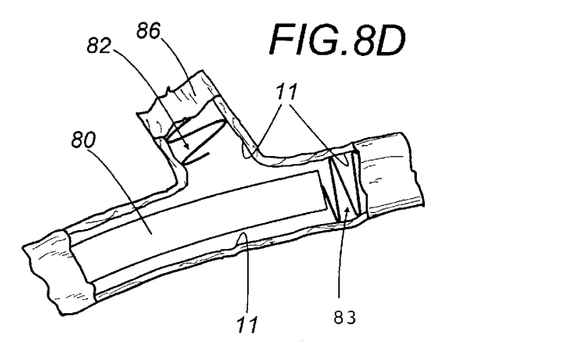
Figure 8E:
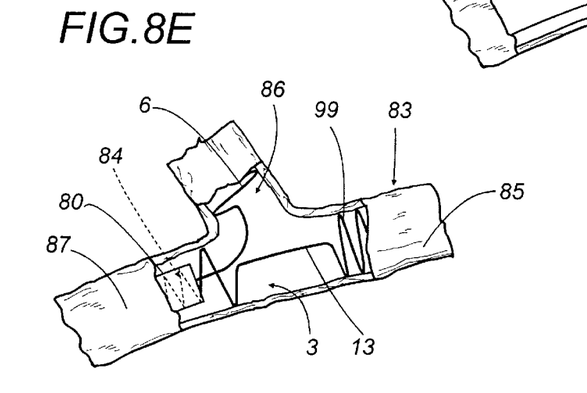

FIGS. 8(A)–8(E) illustrate the sequence by which the bifurcated stents of FIGS. 6 and 7 may be inserted and deployed in a patient's vasculature. FIG. 8A illustrates a bifurcatable stent, such as that shown in FIGS. 6 or 7, loaded into a sleeve 80 at the distal end of a delivery catheter. The sleeve 80 has an open distal end. A push rod 81 associated with the catheter is engageable with the proximal end of the stent within the sleeve. The bifurcated portions of the stent are brought together to a compact tubular configuration having a common access with the remainder of the stent and in that configuration is inserted into the sleeve. The catheter then is advanced and manipulated to locate the sleeve within a first branch 85 of the patient's blood vessel 3 in a position in which the forward section 83 of the stent is to be implanted initially. The sleeve 80 then is retracted from the first branch while the push rod 81 is controlled to effect gradual ejection of the forward section 83 of the stent. The section 83 of the stent then may be stabilized within the stent by expanding the modules on the forward section 83 as described above (expansion means 4 or 5 omitted from FIG. 8 for clarity). With forward section 83 of the stent firmly implanted in place in branch 85 of the blood vessel, the sleeve 80 then is retracted to a location proximally of the juncture of the branch vessel 86. During that further retraction, the section 82 of the stent will have been exposed within the blood vessels and it can be guided into the second branch 86 with the use of conventional guiding elements (not shown) including a variety of catheters or guidewires. With the secondary section 82 in place, the second expansion means 4 or 5 (not shown) is operated to secure and stabilize the section 82 in the branch vessel 86. FIG. 8(D) illustrates an optional subsequent step in which the longitudinal dimension of the stent can be varied particularly in the space 89 between the secondary section 82 and rear section 84. The longitudinally compactable portion 7a, 99 of the wire enables the physician to adjust the longitudinal relative position of the forward section 83 with respect to the rearward section 84. The longitudinal dimension of the stent can be reduced by advancing the sleeve 80 forwardly toward the previously placed forward section 83 thereby compacting longitudinally a portion 99 of the wire 6, 13. After the position has been adjusted as desired, the helical portion 99 may be expanded by the expansion means 4 or 5. After the first and second members have been stabilized, the sleeve 80 is retracted from the third branch 87 of the passage to release the rear section 84 of the stent which then can be stabilized as described.

If desired, the wires embodied in the stent may be coated with a protective material such as carbon or with an anticoagulant substance such as heparin.

In a further alternative embodiment, the stent may be expandable by other means, for example, by forming the module 7 from a shape memory alloy such as nitinol. The stent may be provided with electrical resistance heaters to generate sufficient heat to induce thermally controlled expansion of the shape memory alloy module.

It should be understood that the foregoing description of the invention is intended merely to be illustrative thereof and that other embodiments, modifications and equivalents will be apparent to those skilled in the art without departing from its principles.

I claim:

1. A method for forming a bifurcated stent for placement in a body lumen having a common portion and two branches communicating with the common portion comprising:

providing a first tube-defining member open at each end and having a transverse opening formed between its ends, the tube-defining member being expandable radially from a low profile to an expanded configuration;

providing a second tube-defining member having openings at least at its ends, the second tube-defining member being expandable from a low profile configuration to an expanded configuration;

advancing the second tube into the first tube and through the transverse opening thereby to define a bifurcated configuration; and expanding the second tube from its low profile to an expanded configuration.

2. A method as defined in claim 1 wherein the first tube-defining member is initially in a low profile configuration and is expanded to its expanded configuration before insertion of the second tube-defining member.

3. A method as defined in claim 2 wherein the second tube-defining member is inserted in a low profile and is expanded after forming the bifurcated configuration.

4. A method as defined in any one of the preceding claims wherein the tube-defining members are inelastically expanded.

5. A method as defined in claim 3 wherein each of the tube-defining members has a proximal portion and a distal portion, the proximal portions of the tube-defining members extending longitudinally along a common portion of the stent;

the distal portions of the tube-defining members being separate and adapted to extend independently into branch portions of the body vessel.

6. A method as defined in claim 5 wherein the proximal portion of the first and second tube-defining members are constructed to be complementary to each other and being combinable to cooperatively define a single tubular portion of the bifurcated stent.

7. A method as defined in claim 6 wherein each of the tube defining members comprises an elongate spine having a plurality of tube-defining modules connected thereto in sequential array along the length of the spine, the modules on the proximal portion of each of the tube-defining members being spaced along their respective spines to enable their combination in complementary fashion.

8. A method as defined in claim 7 wherein the transverse opening between the proximal and distal segments of the first tube comprises a space between the proximal and distal portions of the first tube-defining member.

9. A method as defined in claim 7 wherein the spines have substantially greater mass than the modules to enhance their radiographic visibility.

10. A method as defined in claim 1 wherein said assembly of the bifurcated stent is effected in situ within the patient.

11. A method for placing a bifurcated stent in a body lumen having a common portion and two branches communicating with the common portion comprising:

providing a first tube-defining member open at each end and having a transverse opening formed between its ends, the tube-defining member being expandable radially from a low profile to an expanded configuration;

advancing the first member through the body lumen to the branched region with the transverse opening at and exposed to the juncture of the branches of the body lumen;

expanding the first tube-defining member into firm engagement with the inner surface of the common portion and one branch of the body lumen;

providing a second tube-defining member having openings at least at its ends, the second tube-defining member being expandable from a low profile configuration to an expanded configuration;

expanding the first member from its low profile diameter sufficiently to enable it to receive the second member while the second member is in its low profile configuration;

advancing the second member into the first member and through the lateral opening with a portion of the second member extending into the other branch and a portion disposed within the common portion of the body lumen and the first tube-defining member; and expanding the second tube defining member from its low profile to an expanded configuration and into engagement with the lumen of the common portion and the other branch.

12. A method as defined in claim 11 wherein the tube defining members comprise:

an elongate spine;

a plurality of modules connected to the spine at sequential locations along the spine, each module defining a closed circumferential loop, the modules being arranged on the spine to define the tubular member;

the modules being constructed to be expandable from a low profile configuration to an expanded configuration.

13. A method as defined in claim 12 wherein each module is formed from a serpentine wire having a plurality of elongate segments alternated with shorter connective bends, the module being expandable by a balloon disposed within the tubular member such that when the balloon is expanded to cause expansion of the modules, the elongate segments of the modules will spread apart and wipe against the inner luminal surface of the lumen thereby to smooth the surface of the lumen.

14. A method as defined in claim 12 wherein the spine defines a mass substantially greater than that of the modules sufficiently to present a radiographically visual image of the spine when the device is disposed in the body; and positioning the stent within the body lumen by reference to radiographic image of the spine.

15. A bifurcated stent comprising:

a first stent comprising an elongate spine having proximal and distal ends and a plurality of tube-defining modules connected in longitudinal sequence to and along the spine, the modules being arranged to define a proximal group and a distal group, the modules in the proximal group being spaced longitudinally along the spine;

the proximal and distal groups of the tube defining modules on the first stent being spaced from each other to define a lateral opening along the defined tube; and a second stent having proximal and distal ends, the proximal end having a plurality of spaced modules interfitted with the spaced modules in the first group of the first stent, the distal end of the second stent protruding laterally through the opening.

16. A bifurcated stent comprising as defined in claim 15 wherein each module is formed from a serpentine wire having a plurality of elongate segments alternated with shorter connective bends.

17. A bifurcated stent as defined in claim 16 wherein the serpentine wire has free terminal ends and is attached to the spine by a connector.

18. A bifurcated stent as defined in claim 17 wherein the spine comprises a longitudinal support wire and said connectors.

19. A bifurcated stent as defined in claim 18 wherein at least one of the modules or support wire has a malleability different from the other.

20. A bifurcated stent as defined in claim 18 wherein each of the modules, support wire and connectors are formed from a material sufficiently similar in composition to inhibit development of corrosion at their respective junctures.

21. A bifurcated stent as defined in claim 18 further comprising a spacer disposed between adjacent connectors, the spacers being formed from the same material as the connectors, the spacers and connectors defining substantially continuous regions of high radiopacity when visualized radiographically.

22. A bifurcated stent as defined in claim 18 wherein at least the elongate support wire is formed from a non-metallic material.

23. A bifurcated stent as defined in claim 22 wherein the non-metallic material comprises a polymeric material.

24. A bifurcated stent as defined in claim 23 wherein the material comprises nylon.

25. A bifurcated stent as defined in claim 23 wherein the material for the elongate support wire comprises a bioabsorbable material.

26. A bifurcated stent as defined in claim 17 wherein the end modules of the stent are attached to the support wire with the free terminal ends of one end module oriented toward the free terminal ends of the other end module.

27. A bifurcated stent as defined in claim 15 further comprising a second spine connected to at least some of the modules on at least one of the members and extending generally parallel to the first spine.

28. A bifurcated stent as defined in claim 15 wherein the modules are formed from a material belonging to the group comprising annealed stainless steel, titanium alloys, nickel gold alloys, nickel chromium alloys and titanium chromium alloys.

29. A bifurcated stent as defined in claim 15 wherein the stent is coated with a protective material.

30. A bifurcated stent as defined in claim 15 wherein the protective material comprises carbon.

31. A bifurcated stent as defined in claim 15 wherein the bifurcated stent in coated with a drug.

32. A bifurcated stent as defined in claim 31 wherein the drug comprises an anticoagulant.

33. A bifurcated stent as defined in claim 15 wherein the modules are inelastically deformable during expansion.

34. A bifurcated stent as defined in claim 15 dimensioned to be receivable in a human coronary artery while in a low profile configuration and to be expandable within the artery into engagement with the walls of the coronary artery.

35. A bifurcated stent comprising:
 a first elongate support wire;
 a second support wire connected at one end to the first support wire at a junction between the ends of the first support wire, thereby defining a proximal portion on one side of the juncture and a pair of branched portions on the other side of the juncture;
 a plurality of tube-defining modules connected to the support wire proximally of the juncture and to each of the branch portions of the support wires;
 the tube-defining modules on the branch portions of the support wire being disposed at spaced intervals along the branch portions of the support wires to enable the modules on the branch wires to be interfitted and to lie along a substantially common axis with the axis defined by the modules on the proximal portion of the first support wire whereby the bifurcated stent may be compacted into a substantially single tubular configuration insertable into a delivery sheath.

36. A bifurcated stent as defined in 35 further comprising:
 the portion of the second support wire that extends between the juncture and the modules on the second support wire being formed to enable relative longitudinal movement between the modules on the second support wire and the juncture.

37. A bifurcated stent as defined in claim 36 wherein said portion of the second support wire is formed into a helical configuration.

38. A method for placing a bifurcated stent in a bifurcated region of a body lumen comprising:
 providing a stent constructed as defined in either one of claims 36 or 37 further in which a proximal group of modules is connected to the first support wire proximally of the junction, a distal group of modules connected to one of the branch support wires and an intermediate group of modules connected to the other of the branch support wires, the distal and intermediate groups of modules being spaced on their respective support wires to enable the distal and intermediate module groups to be brought together in alignment along a common axis with that of the proximal group of modules;
 compacting the branch portions of the stent to cause the stent to assume a generally singular tubular configuration;
 loading the compacted stent into the distal end of a sheath of a delivery catheter;
 advancing the delivery catheter to the site where the stent is to be implanted;
 positioning the sheath so that the distal group of modules on the second support wire are disposed in one branch of the body lumen, the next proximal group of modules is disposed in the region of the juncture of the branches of the body lumen and the more proximal group of modules is disposed in the common portion of the body lumen;
 withdrawing the sheath while maintaining the position of the stent sufficiently to expose the distal group of modules in one of the branches of the body lumen;
 expanding the distal group of modules into firm engagement with the branch of the body lumen;
 withdrawing further the sheath to expose the intermediate group of modules;
 directing the intermediate group of modules into the other branch of the body lumen;
 expanding the intermediate group of modules into firm engagement with the other branch of the body lumen;
 then withdrawing the sheath further to expose the proximal group of modules within the portion of the body lumen proximal of the branch; and
 expanding the proximal group of modules into firm engagement with the proximal portion of the body lumen.

39. A method as defined in claim 38 further comprising:
 before expanding the proximal group of modules, adjusting the longitudinal position of the proximal group of modules relative to the distal group of modules by adjusting the longitudinal extent of the variable segment of the second support wire.

* * * * *

UNITED STATES PATENT AND TRADEMARK OFFICE
CERTIFICATE OF CORRECTION

PATENT NO.   : 6,033,434
DATED        : March 7, 2000
INVENTOR(S)  : Enzo Borghi Page 1 of 1

It is certified that error appears in the above-identified patent and that said Letters Patent is hereby corrected as shown below:

Column 8,
Line 45, insert after "so" -- that region can be radiographically distinguished. --;

Column 13, claim 30 and 31,
Line 34, delete "15" and insert -- 29 -- therefor;
Line 37, delete "in" and insert -- is -- therefor.

Signed and Sealed this

Twenty-eighth Day of August, 2001

Attest:

NICHOLAS P. GODICI
*Attesting Officer*   *Acting Director of the United States Patent and Trademark Office*